United States Patent
Tu et al.

[11] Patent Number: 5,908,620
[45] Date of Patent: Jun. 1, 1999

[54] TREATMENT FOR DISEASES INVOLVING INFLAMMATION

[75] Inventors: Yuan-Po Tu, Everett, Wash.; Charles G. Irvin, Englewood, Colo.

[73] Assignee: National Jewish Medical and Research Center, Denver, Colo.

[21] Appl. No.: 08/943,567

[22] Filed: Oct. 3, 1997

Related U.S. Application Data

[63] Continuation of application No. 08/382,099, Jan. 31, 1995, Pat. No. 5,674,483.

[51] Int. Cl.$^6$ .......................... A61K 38/20; A61K 45/05
[52] U.S. Cl. .......................... 424/85.2; 424/85.1; 514/2; 514/21; 514/826; 514/851
[58] Field of Search .................. 424/85.1, 85.2; 514/2, 12, 21

[56] References Cited

U.S. PATENT DOCUMENTS

| | | | |
|---|---|---|---|
| 4,944,941 | 7/1990 | Amman | 424/85.5 |
| 4,946,945 | 8/1990 | Wojdani et al. | 530/402 |
| 5,300,292 | 4/1994 | Ulich | 424/85.2 |
| 5,334,379 | 8/1994 | Pillai et al. | 424/85.2 |
| 5,368,854 | 11/1994 | Rennick | 424/85.2 |
| 5,560,915 | 10/1996 | Patterson et al. | 424/275.1 |
| 5,571,515 | 11/1996 | Scott et al. | 424/208.1 |

FOREIGN PATENT DOCUMENTS

WO 90/05147  5/1990  WIPO.
WO 92/05256  4/1992  WIPO.

OTHER PUBLICATIONS

Saloga et al. J. Clin. Invest., 1993 vol. 91, pp. 133–140.
Afonso et al., 1994, Science, 263:235–236.
Heinzel et al., 1993, J. Exp. Med., 177:1505–1509.
Hsieh et al., 1993, Science, 260:547–549.
Sypek et al., 1993, J. Exp. Med., 177:1797–1802.

Primary Examiner—Ponnathapura Achutamurthy
Attorney, Agent, or Firm—Sheridan Ross P.C.

[57] ABSTRACT

The present invention relates to a method to protect an animal from a disease involving inflammation by treating that animal with an effective amount of IL-12. The present invention also relates to a method for prescribing treatment for a respiratory disease involving an inflammatory response and a method for monitoring the success of a treatment for a respiratory disease involving an inflammatory response in an animal. Also included in the present invention is a formulation comprising IL-12 and a compound capable of enhancing the effectiveness of the IL-12 at protecting an animal from a disease involving inflammation.

3 Claims, 3 Drawing Sheets

—◇— IP/OVA + Aero  n=5
—○— IP/OVA + Aero + IL-12  n=6
—□— NIM  n=5

Bl = Baseline
Sl = Saline
Mean Resistance (Rl) ± Standard Error of the Mean (SEM). If no SEM is plotted, SEM is less than the size of the each symbol

FIG. 3

TREATMENT FOR DISEASES INVOLVING INFLAMMATION

This is a continuation of application Ser. No. 08/382,099, filed Jan. 31, 1995, now U.S. Pat. No. 5,674,483, issued Oct. 7, 1997.

This invention was made in part with government support under POI 36577 awarded by the National Institutes of Health. The government has certain rights to this invention.

FIELD OF THE INVENTION

The present invention is related to a method to protect an animal from a disease involving inflammation, in particular, a respiratory disease involving inflammation.

BACKGROUND OF THE INVENTION

Diseases involving inflammation are characterized by the influx of certain cell types and mediators, the presence of which can lead to tissue damage and sometimes death. Diseases involving inflammation are particularly harmful when they afflict the respiratory system, resulting in obstructed breathing, hypoxemia, hypercapnia and lung tissue damage. Obstructive diseases of the airways are characterized by airflow limitation (i.e., airflow obstruction or narrowing) due to constriction of airway smooth muscle, edema and hypersecretion of mucous leading to increased work in breathing, dyspnea, hypoxemia and hypercapnia. While the mechanical properties of the lungs during obstructed breathing are shared between different types of obstructive airway disease, the pathophysiology can differ.

A variety of inflammatory agents can provoke airflow limitation including allergens, cold air, exercise, infections and air pollution. In particular, allergens and other agents in allergic or sensitized animals (i.e., antigens and haptens) cause the release of inflammatory mediators that recruit cells involved in inflammation. Such cells include lymphocytes, eosinophils, mast cells, basophils, neutrophils, macrophages, monocytes, fibroblasts and platelets. Inflammation results in airway hyperresponsiveness. A variety of studies have linked the degree, severity and timing of the inflammatory process with the degree of airway hyperresponsiveness. Thus, a common consequence of inflammation is airflow limitation and/or airway hyperresponsiveness.

Currently, therapy for treatment of inflammation predominantly involves the use of glucocorticosteroids. Other anti-inflammatory agents are used including cromolyn and nedocromil. Symptomatic treatment with beta-agonists, anticholinergic agents and methyl xanthines are clinically beneficial for the relief of discomfort but fail to stop the underlying inflammatory processes that cause the disease. The frequently used systemic glucocorticosteroids have numerous side effects, including, but not limited to, weight gain, diabetes, hypertension, osteoporosis, cataracts, atherosclerosis, increased susceptibility to infection, increased lipids and cholesterol, and easy bruising. Aerosolized glucocorticosteroids have fewer side effects but can be less potent and have side effects, such as thrush.

Other anti-inflammatory agents, such as cromolyn and nedocromil are much less potent and have fewer side effects. Anti-inflammatory agents that are primarily used as immunosuppressive agents and anti-cancer agents (i.e., cytoxan, methotrexate and Immuran) have also been used to treat inflammation. These agents, however, have serious side effect potential, including, but not limited to, increased susceptibility to infection, liver toxicity, drug-induced lung disease, and bone marrow suppression. Thus, such drugs have found limited clinical use for the treatment of most airway hyperresponsiveness lung diseases.

The use of anti-inflammatory and symptomatic relief reagents is a serious problem because of their side effects or their failure to attack the underlying cause of an inflammatory response. There is a continuing requirement for less harmful and more effective reagents for treating inflammation. Thus, there remains a need for processes using natural (i.e., non-synthetic) reagents with lower side effect profiles and less toxicity than current anti-inflammatory therapies.

SUMMARY OF THE INVENTION

The present invention provides for a method and a formulation for protecting an animal from diseases involving inflammation. The present invention is particularly advantageous in that it provides for a the use of a natural substance that is not a synthetically-derived drug, thereby reducing the side effects and toxicity profiles frequently associated with anti-inflammatory therapies.

One embodiment of the present invention includes a method to protect an animal from a disease involving an inflammatory response, the method comprising administering to the animal an effective amount of interleukin-12. The method of the present invention is particularly effective in protecting animals from lung diseases caused by inflammation and skin diseases caused by inflammation. Preferably, the animal is desensitized to a disease by administering the interleukin-12. In particular, an animal is desensitized against an antigen, an allergen, a hapten, a drug and/or an occupational asthma causing agent.

Another embodiment of the present invention is a method for prescribing treatment for a respiratory disease involving an inflammatory response, comprising: (1) administering to an animal an effective amount of interleukin-12; (2) measuring a change in lung function in response to a provoking agent in the animal to determine if the interleukin-12 is capable of modulating airway hyperresponsiveness; and (3) prescribing a pharmacological therapy effective to reduce inflammation based upon the changes in lung function. Preferred provoking agents include direct and indirect stimuli.

Yet another embodiment of the present invention includes a method for monitoring the success of a treatment for a respiratory disease involving an inflammatory response in an animal, the method comprising: (1) administering an effective amount of interleukin-12 to an animal that has been treated for a respiratory disease involving an inflammatory response; (2) measuring a change in lung function in the animal in response to a provoking agent; and (3) monitoring the success of the treatment by comparing the change in lung function with previous measurements of lung function in the animal.

The present invention also includes a formulation for protecting an animal from a disease involving inflammation, comprising interleukin-12 and an allergen, an antigen, a hapten, IL-2, IL-4, glucocorticosteroids, anti-cyclooxygenase agents, anti-cholinergic agents, beta-adrenergic agonists, methyl xanthines, anti-histamines, cromones, zyleuton, anti-CD4 reagents, anti-IL-5 reagents, surfactants, anti-thromboxane reagents, anti-serotonin reagents, ketotiphen, cytoxin, cylosporin, methotrexate, macrolide antibiotics, troleadomycin, heparin, and/or low molecular weight heparins.

DETAILED DESCRIPTION OF THE INVENTION

One embodiment of the present invention is a method to protect an animal from a disease involving inflammation, comprising administering to the animal an effective amount of interleukin-12 (IL-12). The inventors have discovered that IL-12 is a significant inhibitor of inflammation. Previous investigators have reported the use of IL-12 in diseases including bacterial, viral and parasitic infections, anemia, T and B cell deficiencies and tumorigenesis (Trinchieri et al., PCT Publication No. WO 92/05256, published Apr. 2, 1992; Trinchieri et al., PCT Publication No. WO 92/05147, published May 17, 1990; Afonso et al., pp. 235–236, 1994, Science, Vol. 263, January 14; Sypek et al., pp. 1797–1802, 1993, J. Exp. Med., Vol. 177, June; Heinzel et al., pp. 1505–1509, 1993, J. Expt. Med., Vol. 177, May; and Hsieh et al., pp. 547–549, 1993, Science, Vol. 260, April 23). Such reports, however, do not disclose the use of IL-12 to treat diseases involving inflammation which can involve different cellular and humoral responses than the diseases in the reports.

According to the present invention, IL-12 can be administered to any member of the kingdom Animalia including, without limitation, primates, rodents, livestock and domestic pets. A preferred animal to protect using IL-12 includes a human, a cat and a horse. A preferred horse to protect with IL-12 includes a racehorse or a showhorse.

As used herein, the phrase "to protect an animal from a disease involving inflammation" refers to reducing the potential for an inflammatory response (i.e., a response involving inflammation) to an inflammatory agent (i.e., an agent capable of causing an inflammatory response, e.g., methacholine, histamine, an allergen, a leukotriene, saline, hyperventilation, exercise, sulfur dioxide, adenosine, propranolol, cold air, antigen and bradykinin). Preferably, the potential for an inflammatory response is reduced, optimally, to an extent that the animal no longer suffers discomfort and/or altered function from exposure to the inflammatory agent. For example, protecting an animal can refer to the ability of a compound, when administered to the animal, to prevent a disease from occurring and/or cure or alleviate disease symptoms, signs or causes. In particular, protecting an animal refers to modulating an inflammatory response to suppress (e.g., reduce, inhibit or block) an overactive or harmful inflammatory response. Also in particular, protecting an animal refers to regulating cell-mediated immunity and/or humoral immunity (i.e., T cell activity and/or IgE activity). Disease refers to any deviation from normal health of an animal and include disease symptoms as well as conditions in which a deviation (e.g., infection, gene mutation, genetic defect, etc.) has occurred but symptoms are not yet manifested.

In a preferred embodiment, the present invention protects an animal from includes a lung disease caused by inflammation or a skin disease caused by inflammation (e.g., atopic dermatitis). In a more preferred embodiment, the present invention protects an animal from includes a chronic obstructive pulmonary disease (COPD) of the airways (i.e., airway obstruction caused by infiltration of inflammatory cells, scarring, edema, smooth muscle hypertrophy/hyperplasia, smooth muscle contraction and narrowing due to secretions, e.g., mucous, by cells). In an even more preferred embodiment, the present invention protects an animal from includes asthma, allergic bronchopulmonary aspergillosis, hypersensitivity pneumonia, eosinophilic pneumonia, emphysema, bronchitis, allergic bronchitis bronchiectasis, cystic fibrosis, hypersensitivity pneumonitis, occupational asthma (i.e., asthma, wheezing, chest tightness and cough caused by a sensitizing agent, such as an allergen, irritant or hapten, in the work place), sarcoid, reactive airway disease syndrome (i.e., a single exposure to an agent that leads to asthma), interstitial lung disease, hyper-eosinophilic syndrome or parasitic lung disease. In a preferred embodiment, the present invention protects an animal from asthma, occupational asthma and reactive airway disease syndrome.

Preferably, protecting an animal from a disease involving inflammation includes desensitizing an animal by administering an effective amount of IL-12 to the animal. As used herein, desensitizing an animal refers reducing the animal's immune response to a particular compound capable of causing an inflammatory response. Desensitizing an animal against a particular compound can include immunizing or tolerizing to a particular compound. Immunization refers to stimulating an immune response by, for example, activating T helper cells to secrete cytokines which stimulate immunoglobulin production by B cells. Tolerizing refers to inhibiting an immune response by, for example, killing or anergizing (i.e., diminishing reactivity by a T cell to an antigenic peptide) particular cells involved in the immune response.

Suitable agents against which to desensitize an animal against include compounds capable of causing inflammation. Preferred compounds against which to desensitize an animal against include, but are not limited to, an allergen, an antigen, a hapten, a drug and/or an occupational asthma causing agent. An allergen refers a compound capable of inducing an allergic or hypersensitive response. An antigen refers to a compound (i.e., a foreign substance) that binds specifically to an antibody or a T cell receptor and elicits an immune response. A hapten refers to a low molecular weight compound that is not immunogenic by itself, but, when complexed or coupled to a larger carrier molecule (i.e., a high molecular weight protein), can elicit antibodies directed against the hapten. A drug refers to any chemical compound that can be administered to an animal as an aid in the diagnosis, treatment or prevention of disease or an abnormal condition. An occupational asthma causing agent refers to an agent encountered in a workplace environment that is capable of causing airway obstruction. Such agents can include allergens, antigens and haptens. Occupational asthma causing agents that are haptens include, but are not limited to, benzene derivatives (e.g., aminobenzenes, aminobenzoic acid), toluidine, toluidine derivatives (e.g., toluidine diisocyanate) metals, amines, acid anhydrides and plicatic acid. Other occupational asthma causing agents include, for example, cigarette smoke, particulate pollution, chemical vapors, dyes, wood dust, vegetable gums solder and enzymes from foods, molds, fungi, bacteria and their by-products, detergents and pharmaceutical reagents.

In accordance with the present invention, acceptable protocols to administer IL-12 include the mode of administration and the effective amount of IL-12 administered to an animal, including individual dose size, number of doses and frequency of dose administration. Determination of such protocols can be accomplished by those skilled in the art.

Suitable modes of administration can include, but are not limited to, oral, nasal, topical, transdermal, rectal, and parenteral routes. Preferred parenteral routes can include, but are not limited to, subcutaneous, intradermal, intravenous, intramuscular and intraperitoneal routes. Preferred topical routes include inhalation by aerosol (i.e., spraying) or topical surface administration to the skin of an animal.

According to the method of the present invention, an effective amount of IL-12 to administer to an animal comprises an amount that is capable of reducing airway hyper-responsiveness (AHR) and/or reducing airflow limitation and/or symptoms (e.g., shortness of breath, wheezing, dyspnea, exercise limitation or nocturnal awakenings), without being toxic to the animal. An amount that is toxic to an animal comprises any amount that causes damage to the structure or function of an animal (i.e., poisonous). AHR refers to an abnormality of the airways that allows them to narrow too easily and/or too much in response to a stimulus capable of inducing airflow limitation. AHR can be a functional alteration of the respiratory system caused by inflammation. Airflow limitation refers to narrowing of airways that can be irreversible or reversible. Airflow limitation can be caused by bronchospasm, airway smooth muscle hypertrophy, airway smooth muscle contraction, mucous secretion, cellular deposits, epithelial destruction, alteration to epithelial permeability, alterations to smooth muscle function or sensitivity, abnormalities of the lung parenchyma and infiltrative diseases in and around the airways.

AHR can be measured by a stress test that comprises measuring an animal's respiratory system function in response to a provoking agent (i.e., stimulus). AHR can be measured as a change in respiratory function from baseline plotted against the dose of a provoking agent (a procedure for such measurement is described in detail below in the Examples). Respiratory function can be measured by, for example, spirometry, plethysmographically, peak flows, symptom scores, physical signs (i.e., respiratory rate), wheezing, exercise tolerance, use of rescue medication (i.e., bronchodialators) and blood gases. In humans, spirometry can be used to gauge the change in respiratory function in conjunction with a provoking agent, such as methacholine or histamine. In humans, spirometry is performed by asking a person to take a deep breath and blow, as long, as hard and as fast as possible into a gauge that measures airflow and volume. The volume of air expired in the first second is known as forced expiratory volume ($FEV_1$) and the total amount of air expired is known as the forced vital capacity (FVC). In humans, normal predicted $FEV_1$ and FVC are available and standardized according to weight, height, sex and race. An individual free of disease has an $FEV_1$ and a FVC of at least about 80% of normal predicted values for a particular person and a ratio of $FEV_1/FVC$ of at least about 80%. Values are determined before (i.e, representing an animal's resting state) and after (i.e., representing an animal's higher lung resistance state) inhalation of the provoking agent. The position of the resulting curve indicates the sensitivity of the airways to the provoking agent.

The effect of increasing doses or concentrations of the provoking agent on lung function is determined by measuring the forced expired volume in 1 second ($FEV_1$) and $FEV_1$ over forced vital capacity ($FEV_1/FVC$ ratio) of the animal challenged with the provoking agent. In humans, the dose or concentration of a provoking agent (i.e., methacholine or histamine) that causes a 20% fall in $FEV_1$ ($PD_{20}FEV_1$) is indicative of the degree of AHR. $FEV_1$ and FVC values can be measured using methods known to those of skill in the art.

A variety of provoking agents are useful for measuring AHR values. Suitable provoking agent include direct and indirect stimuli. Preferred provoking agents include, for example, methacholine (Mch), histamine, an allergen, a leukotriene, saline, hyperventilation, exercise, sulfur dioxide, adenosine, propranolol, cold air, antigen, bradykinin and mixtures thereof. Preferably, Mch is used as a provoking agent. Preferred concentrations of Mch to use in a concentration-response curve are between about 0.001 and about 100 milligram per milliliter (mg/ml). More preferred concentrations of Mch to use in a concentration-response curve are between about 0.01 and about 50 mg/ml. Even more preferred concentrations of Mch to use in a concentration-response curve are between about 0.02 and about 25 mg/ml. When Mch is used as a provoking agent, the degree of AHR is defined by the provocative concentration of Mch needed to cause a 20% drop of the $FEV_1$ of an animal ($PC_{20methacholine}FEV_1$). For example, in humans and using standard protocols in the art, a normal person typically has a $PC_{20methacholine}FEV_1 > 8$ mg/ml of Mch. Thus, in humans, AHR is defined as $PC_{20methacholine}FEV_1 < 8$ mg/ml of Mch.

The effectiveness of a drug to protect an animal from AHR in an animal having or susceptible to AHR is measured in doubling amounts. For example, the effectiveness an animal to be protected from AHR is significant if the animal's $PC_{20methacholine}FEV_1$ is at 1 mg/ml before administration of the drug and is at 2 mg/ml of Mch after administration of the drug. Similarly, a drug is considered effective if the animal's $PC_{20methacholine}FEV_1$ is at 2 mg/ml before administration of the drug and is at 4 mg/ml of Mch after administration of the drug.

In one embodiment of the present invention, an effective amount of IL-12 to administer to an animal includes an amount that is capable of decreasing methacholine responsiveness without being toxic to the animal. A preferred effective amount of IL-12 comprises an amount that is capable of increasing the $PC_{20methacholine}FEV_1$ of an animal treated with the interleukin-12 by about one doubling concentration towards the $PC_{20methacholine}FEV_1$ of a normal animal. A normal animal refers to an animal known not to suffer from or be susceptible to abnormal AHR. A test animal refers to an animal suspected of suffering from or being susceptible to abnormal AHR.

In another embodiment, an effective amount of IL-12 according to the method of the present invention, comprises an amount that results in an improvement in an animal's $PC_{20methacholine}FEV_1$ value such that the $PC_{20methacholine}FEV_1$ value obtained before administration of the IL-12 when the animal is provoked with a first concentration of methacholine is the same as the $PC_{20methacholine}FEV_1$ value obtained after administration of the IL-12 when the animal is provoked with double the amount of the first concentration of methacholine. A preferred amount of IL-12 comprises an amount that results in an improvement in an animal's $PC_{20methacholine}FEV_1$ value such that the $PC_{20methacholine}FEV_1$ value obtained before administration of the IL-12 is between about 0.01 mg/ml to about 8 mg/ml of methacholine is the same as the $PC_{20methacholine}FEV_1$ value obtained after administration of the IL-12 is between about 0.02 mg/ml to about 16 mg/ml of methacholine.

According to the present invention, respiratory function can be evaluated with a variety of static tests that comprise measuring an animal's respiratory system function in the absence of a provoking agent. Examples of static tests include, for example, spirometry, plethysmographically, peak flows, symptom scores, physical signs (i.e., respiratory rate), wheezing, exercise tolerance, use of rescue medication (i.e., bronchodialators) and blood gases. Evaluating pulmonary function in static tests can be performed by measuring, for example, Total Lung Capacity (TLC), Thoracic Gas Volume (TgV), Functional Residual Capacity (FRC), Residual Volume (RV) and Specific Conductance (SGL) for lung volumes, Diffusing Capacity of the Lung for Carbon Monoxide (DLCO), arterial blood gases, including pH, $P_{O2}$ and $P_{CO2}$ for gas exchange. Both $FEV_1$ and $FEV_1/FVC$ can be used to measure airflow limitation. If spirometry is used in humans, the $FEV_1$ of an individual can be compared to the $FEV_1$ of predicted values. Predicted $FEV_1$ values are available for standard normograms based on the animal's age, sex, weight, height and race. A normal animal typically has an $FEV_1$ at least about 80% of the predicted $FEV_1$ for the animal. Airflow limitation results in a $FEV_1$ less than 80% of predicted values. An alternative method to measure airflow limitation is based on the ratio of $FEV_1$ and FVC ($FEV_1/FVC$). Disease free individuals are defined as having a $FEV_1/FVC$ ratio of at least about 80%. Airflow obstruction causes the ratio of $FEV_1/FVC$ to fall to less than 80% of predicted values. Thus, an animal having airflow limitation is defined by an $FEV_1/FVC$ less than about 80%.

The effectiveness of a drug to protect an animal having or susceptible to airflow limitation is determined by measuring the percent improvement in $FEV_1$ and/or the $FEV_1/FVC$ ratio before and after administration of the drug. In one embodiment, an effective amount of IL-12 comprises an amount that is capable of reducing the airflow limitation of an animal such that the $FEV_1/FVC$ value of the animal is at least about 80%. In another embodiment, an effective amount of IL-12 comprises an amount that improves an animal's $FEV_1$ preferably by between about 6% and about 100%, more preferably by between about 7% and about 100%, and even more preferably by between about 8% and about 100% of the animal's predicted $FEV_1$.

It is within the scope of the present invention that a static test can be performed before or after administration of a provocative agent used in a stress test.

In another embodiment, an effective amount of IL-12 for use with the method of the present invention, comprises an amount that is capable of reducing the airflow limitation of an animal such that the variation of $FEV_1$ values of the animal when measured in the evening before bed and in the morning upon waking is less than about 75%, preferably less than about 45%, more preferably less than about 15%, and even more preferably less than about 8%.

In yet another embodiment, an effective amount of IL-12 for use with the method of the present invention, comprises an amount that reduces the level of IgE in the serum of an animal to between about 0 to about 100 international units/ ml, preferably between about 10 to about 50 international units/ml, more preferably between about 15 to about 25 international units/ml, and even more preferably about 20 international units/ml. The concentration of IgE in the serum of an animal can be measured using methods known to those of skill in the art. In particular, the concentration of IgE in the serum of an animal can be measured by, for example, using antibodies that specifically bind to IgE in an enzyme-linked immunoassay or a radioimmunoassay.

In another embodiment, an effective amount of IL-12 for use with the method of the present invention, comprises an amount that reduces eosinophil blood counts in an animal to preferably between about 0 and 470 cells/mm$^3$, more preferably to between about 0 and 300 cells/mm$^3$, and even more preferably to between about 0 and 100 cells/mm$^3$. Eosinophil blood counts of an animal can be measured using methods known to those of skill in the art. In particular, the eosinophil blood counts of an animal can be measured by vital stains, such as phloxin B or Diff Quick.

A suitable single dose of IL-12 to administer to an animal is a dose that is capable of protecting an animal from an inflammatory response when administered one or more times over a suitable time period. In particular, a suitable single dose of IL-12 comprises a dose that improves AHR by a doubling dose of a provoking agent or improves the static respiratory function of an animal. A preferred single dose of IL-12 comprises between about 1 microgram×kilogram$^{-1}$ and about 10 milligram×kilograms$^{-1}$ body weight of an animal. A more preferred single dose of IL-12 comprises between about 5 microgram×kilogram$^{-1}$ and about 7 milligram×kilogram$^{-1}$ body weight of an animal. An even more preferred single dose of IL-12 comprises between about 10 microgram×kilogram$^{-1}$ and about 5 milligram× kilogram$^{-1}$ body weight of an animal. A particularly preferred single dose of IL-12 comprises between about 0.1 milligram×kilogram$^{-1}$ and about 5 milligram×kilogram$^{-1}$ body weight of an animal, if the IL-12 is delivered by aerosol. Another particularly preferred single dose of IL-12 comprises between about 0.1 microgram×kilogram$^{-1}$ and about 10 microgram×kilogram$^{-1}$ body weight of an animal, if the IL-12 is delivered parenterally.

A preferred IL-12 for use with the method of the present invention, including homologues thereof, is capable of regulating the growth of natural killer (NK) and/or T cells. In addition, a preferred IL-12 for use with the method of the present invention, including homologues thereof, is capable of increasing antibody derived cytotoxicity or cell-mediated NK cell cytotoxicity. A preferred IL-12 homologue includes at least one epitope capable of regulating the growth of natural killer (NK) and/or T cells substantially similar to that of a natural IL-12 counterpart. The ability of an IL-12 homologue to regulate the growth of NK and/or T cells can be tested using techniques known to those skilled in the art including cellular assays that determine the growth of NK cells or T cells in tissue culture.

In one embodiment, IL-12 suitable for use with the method of the present invention comprises IL-12 derived from a substantially similar species of animal to which the IL-12 is to be administered. For example, if IL-12 is to be administered to a human patient, then preferably primate, and more preferably human IL-12 can be used to protect the animal from a disease involving inflammation. If IL-12 is to be administered to a mouse, then preferably rodent (i.e., hamster, rat, guinea pig), and more preferably mouse IL-12 can be used. Preferred IL-12 of the present invention includes IL-12 derived from primates and rodents. More preferred IL-12 includes IL-12 derived from humans and mice, with human IL-12 being even more preferred.

In another embodiment, IL-12 suitable for use with the method of the present invention comprises an isolated protein which has been removed from its natural milieu. Isolated IL-12 can, for example, be obtained from its natural source, be produced using recombinant DNA technology, or be synthesized chemically. Preferably, IL-12 of the present invention includes recombinantly produced IL-12.

In yet another embodiment, IL-12 suitable for use with the method of the present invention comprises IL-12 having sufficient activity to stimulate blast cell proliferation up to half-maximal in a PHA blast cell proliferation assay using RB012892 (*J. Exp. Med.* 177:1797–1802, 1993). Preferably, IL-12 of the present invention have an activity of from about $1 \times 10^6$ to about $6 \times 10^6$ units/mg, more preferably about $2 \times 10^6$ to about $5 \times 10^6$ units/mg and even more preferably about $4 \times 10^6$ units/mg when measured by the above-referenced blast cell proliferation assay.

In another embodiment, IL-12 of the present invention can be administered simultaneously or sequentially with an effective amount of a compound capable of enhancing the ability of the IL-12 to protect an animal from a disease involving inflammation. The present invention also includes a formulation containing IL-12 and at least one such compound to protect an animal from a disease involving inflammation. A suitable compound to be administered simultaneously or sequentially with IL-12 includes a compound that is capable of regulating IgE production (i.e., suppression of interleukin-4 induced IgE synthesis), regulating interferon-gamma production, regulating NK cell proliferation and activation, regulating lymphokine activated killer cells (LAK), regulating T helper cell activity, regulating degranulation of mast cells, protecting sensory nerve endings, regulating eosinophil and/or blast cell activity, preventing or relaxing smooth muscle contraction, reduce microvascular permeability and Th1 and/or Th2 T cell subset differentiation. A preferred compound to be administered simultaneously or sequentially with IL-12 includes, but is not limited to, an antigen, an allergen (e.g., plant, such as weed, grass, tree, peanut; animal, such as cat; bacterial; parasitic, such as mite and flea; and metal-based allergens), a hapten and a drug. A preferred drug to be administered simultaneously or sequentially with IL-12 includes, but is not limited to, IL-2, IL-4, anti-IL-4 reagents, glucocorticosteroids, anti-cyclooxygenase agents, anti-cholinergic agents beta-adrenergic agonists, methyl xanthines (i.e, theophylline), anti-histamines, cromones (i.e., chromoglycate), zyleuton, anti-CD4 reagents, anti-IL-5 reagents, surfactants, anti-thromboxane reagents, anti-serotonin reagents, ketotiphen, cytoxin, cylosporin, methotrexate, macrolide antibiotics, troleadomycin, heparin, low molecular weight heparin, and mixtures thereof. The choice of compound to be administered in conjunction with IL-12 can be made by one of skill in the art based on various characteristics of the animal. In particular, an animal's genetic background, history of occurrence of inflammation, dyspnea, wheezing upon physical exam, symptom scores, physical signs (i.e., respiratory rate), exercise tolerance, use of rescue medication (i.e., bronchodialators) and blood gases.

A formulation of the present invention can also include other components such as a pharmaceutically acceptable excipient. For example, formulations of the present invention can be formulated in an excipient that the animal to be protected can tolerate. Examples of such excipients include water, saline, phosphate buffered solutions, Ringer's solution, dextrose solution, Hank's solution, polyethylene glycol-containing physiologically balanced salt solutions, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability or buffers. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, IL-12 or a formulation of the present invention can include a controlled release composition that is capable of slowly releasing the IL-12 or formulation of the present invention into an animal. As used herein a controlled release composition comprises IL-12 or a formulation of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release compositions of the present invention include liquids that, upon administration to an animal, form a solid or a gel in situ. Preferred controlled release compositions are biodegradable (i.e., bioerodible).

A preferred controlled release composition of the present invention is capable of releasing IL-12 or a formulation of the present invention into the blood of an animal at a constant rate sufficient to attain therapeutic dose levels of IL-12 or the formulation to prevent inflammation over a period of time ranging from days to months based on IL-12 toxicity parameters. A controlled release formulation of the present invention is capable of effecting protection for preferably at least about 6 hours, more preferably at least about 24 hours, and even more preferably for at least about 7 days.

Another embodiment of the present invention comprises a method for prescribing treatment for a respiratory disease involving an inflammatory response, the method comprising: (1) administering to an animal an effective amount of IL-12; (2) measuring a change in lung function in response to a provoking agent in the animal to determine if the IL-12 is capable of modulating a disorder selected from the group consisting of airway hyperresponsiveness; and (3) prescribing a pharmacological therapy effective to reduce inflammation based upon the changes in lung function. A change in lung function includes measuring static respiratory function before and after administration of IL-12. In accordance with the present invention, the animal receiving the IL-12 is known to have a respiratory disease involving inflammation. Measuring a change in lung function in response to a provoking agent can be done using a variety of techniques known to those of skill in the art. In particular, a change in lung function can be measured by determining the $FEV_1$, $FEV_1/FVC$, $PC_{20methacholine}FEV_1$ and/or peak flow for the recipient of the provoking agent. Other methods to measure a change in lung function include, for example, lung volumes, peak flows, symptom scores, physical signs (i.e., respiratory rate), wheezing, exercise tolerance, use of rescue medication (i.e., bronchodilators) and blood gases. A suitable pharmacological therapy effective to reduce inflammation in an animal can be evaluated by determining if and to what extent the administration of IL-12 has an effect on the lung function of the animal. If a change in lung function results from the administration of IL-12, then that animal can be treated with IL-12. In addition or depending upon the extent of change in lung function, additional compounds can be administered to the animal to enhance the treatment of the animal. If no change or a sufficiently small change in lung function results from the administration of IL-12, then that animal should be treated with an alternative compound to IL-12. The present method for prescribing treatment for a respiratory disease can also include evaluating other characteristics of the patient, such as the patient's history of respiratory disease, the presence of infectious agents, the patient's habits (e.g., smoking), the patient's working and living environment, allergies, a history of life threatening respiratory events, severity of illness, duration of illness (i.e., acute or chronic), and previous response to other drugs and/or therapy.

Another embodiment of the present invention comprises a method for monitoring the success of a treatment for a respiratory disease involving an inflammatory response in an animal, the method comprising: (1) administering an effective amount of interleukin-12 to an animal that has been treated for a respiratory disease involving an inflammatory response; (2) measuring a change in the lung function of the animal in response to a provoking agent of the present invention; and (3) monitoring the success of the treatment by comparing the change in lung function with previous measurements of lung function in the animal. If the treatment does not result in the improvement of lung function, then the administration of IL-12 should be able to alter lung function Conversely, if the treatment does result in lung function improvement, then the administration of IL-12 should not alter lung function because the lung function will have been improved by the original treatment. The monitoring of success can also include comparing the change in lung function before and after administration of IL-12 to an animal with other aforementioned characteristics of the animal.

Another embodiment of the present invention includes a method for long-term care of a patient having a disease involving inflammation, the method comprising: (1) assessing the status of the disease of a patient; (2) administering to the patient an effective amount of IL-12; and (3) providing long-term care of the patient by preventing significant exposure of the patient to the cause of the disease. Preferably, the status of the disease is assessed by determining a characteristic of the disease, such as determining the form, severity and complications of the disease. In addition, the status of the disease is assessed by determining, for example, a causative agent and/or a provoking agent of the disease. From the assessment of the causative and/or provoking agent of the disease, long-term care can be provided by minimizing the exposure of the patient to the causative and/or provoking agent of the disease.

The following examples are provided for the purposes of illustration and are not intended to limit the scope of the present invention.

EXAMPLES

Example 1

This example describes the effect of administration IL-12 to BALB/c mice immunized with ovalbumin using alum as an adjuvant.

A. Experiment 1

Airway hyperresponsiveness was assessed in mice (i.e., stress tests) in the following manner. Six to 8 week old BALB/c female mice, weighing about 18–25 grams, were obtained from Jackson Laboratories (Bar Harbor, Minn.). The mice were quarantined for 2–3 weeks. The mice were then bled and the blood was assayed for the presence of antibody to common murine viruses (e.g., Minute virus, hepatitis virus, mycoplasma pulmonis, pneumonia virus and sendai virus) using methods standard in the art. After the mice were established to be virus free, the mice were housed on cedar chips (J. P. Murphy Forest Products, Montville, N.J.), in micro isolators (Allentown Caging Equipment, Co., Allentown, N.J.) placed in HEPA flow hoods (NuAire Animal Isolators, Plymouth, Minn.) using standard barrier techniques. The mice were allowed free access to water and fed Purina's 5L31 Pico Rodent Chow (Ralston Purina, St. Louis, Mo.) ab Yibra.

Eleven mice (IP/OVA) were injected intraperitoneally with about 10 $\mu$g ovalbumin (OVA) (Sigma, St. Louis, Mo.) in 100 $\mu$g aluminum hydroxide (Alum) (T. J. Baker Chemical Co., Phillipsburg, N.J.) dissolved in phosphate buffered saline (PBS). Five mice that were housed under identical conditions as described above did not receive any treatments and are referred to herein as non-immune (NIM) mice.

Two weeks after priming, the 11 OVA injected mice were exposed to a 1% aerosolized solution of OVA in PBS for 30 minutes daily for 8 days (i.e., 8 exposures in 8 days) and are referred to herein as IP/OVA+AERO. Six of the 11 mice were treated with 1 $\mu$g of murine recombinant IL-12 intraperitoneally (IP) one hour before each of the 8 daily aerosolized OVA treatments.

Twenty four hours following the last aerosol exposure, the mice were attached to the following equipment to measure the respiratory function of each mouse when challenged with a provoking agent. The mice were anesthetized with 70 mg/kg of intraperitoneal pentobarbital sodium (Abbott Laboratories, Chicago, Ill.) and the trachea and right internal jugular vein were exposed. A metal 19 gauge endotracheal catheter was inserted and sutured into the trachea, and a 0.0048 cm internal diameter×5 cm Silastic catheter (Dow Corning Corp., Midland, Mich.) was inserted and sutured into the right internal vein. Following surgery, the mice were in a plethysmographic chamber and the tracheostomy tube was attached to a 4-way connector (Small Parts, Inc., Miami Lakes, Fla.), with one port connected to a catheter measuring airway opening pressure ($P_{AO}$) and two ports connected to the inspiratory and expiratory ports of a volume cycled ventilator (Harvard Apparatus Rodent Ventilator, Model 680, South Natwick, Mass.). The mice were ventilated at 200 breaths per minute, tidal volume of 5–6 ml/kg, and with 2 cm $H_2O$ positive end-expiratory pressure. Adequacy of alveolar ventilation was confirmed by the lack of spontaneous respiration (i.e., over-breathing), and transcutaneous $CO_2$ measurements. Transpulmonary pressure was estimated as the $P_{AO}$, referenced to pressure within the plethysmographic using a differential pressure transducer (Validyne Model MP-45-1-871, Validyne Engineering Corp., Northridge, Calif.). Changes in volume were determined by pressure changes in the plethysmographic chamber referenced to pressure in a reference box using a second differential pressure transducer. The two transducers and amplifiers were electronically phased to less than 5 degrees from 1 to 30 Hz and then converted from an analog to digital signal using a 16 bit analog to digital board Model NB-MIO-16X-18 (National Instruments Corp., Austin, Tex.) at 600 bits per second per channel. The digitized signals were fed into a Macintosh Quadra 800 computer (Model M1206, Apple Computer, Inc., Cupertino, Calif.) and analyzed using the real time computer program LabVIEW (National Instruments Corp., Austin, Tex.). Flow was determined by differentiation of the volume signal and compliance was calculated as the change in volume divided by the change in pressure at zero flow points for the inspiratory phase and expiratory phase. Average compliance was calculated as the arithmetic mean of inspiratory and expiratory compliance for each breath. The LabVIEW computer program used pressure, flow, volume and average compliance to calculate pulmonary resistance (Rl) and compliance according to the method of Amdur et al. (pp. 364–368, 1958, *Am. J. Physiol.*, vol. 192). The breath by breath results for Rl, compliance, conductance and specific compliance were tabulated and the reported values are the average of at least 10–20 breaths at the peak of response for each dose.

Following placement in a plethysmographic chamber, each mouse was challenged with methacholine to assess airway hyperresponsive pulmonary function. In vivo airway hyperresponsiveness (AHR) was assessed as the change in respiratory system function after noncumulative, intravenous methacholine (i.e., Acetyl-β-methylcholine) challenge (McDRC). Acetyl-β-methylcholine (Aldrich Chemical, Milwaukee, Wis.) was dissolved in normal saline and administered into the internal jugular vein catheter with a micro syringe (Hamilton, Co., Reno, Nev.). AHR was assessed as the resistance (Rl) in $cmH_2O/ml/sec$ following administration of 6 tripling doses of about 5 μg/mg to about 1233 μg/mg of intravenous methacholine.

Figure 1:
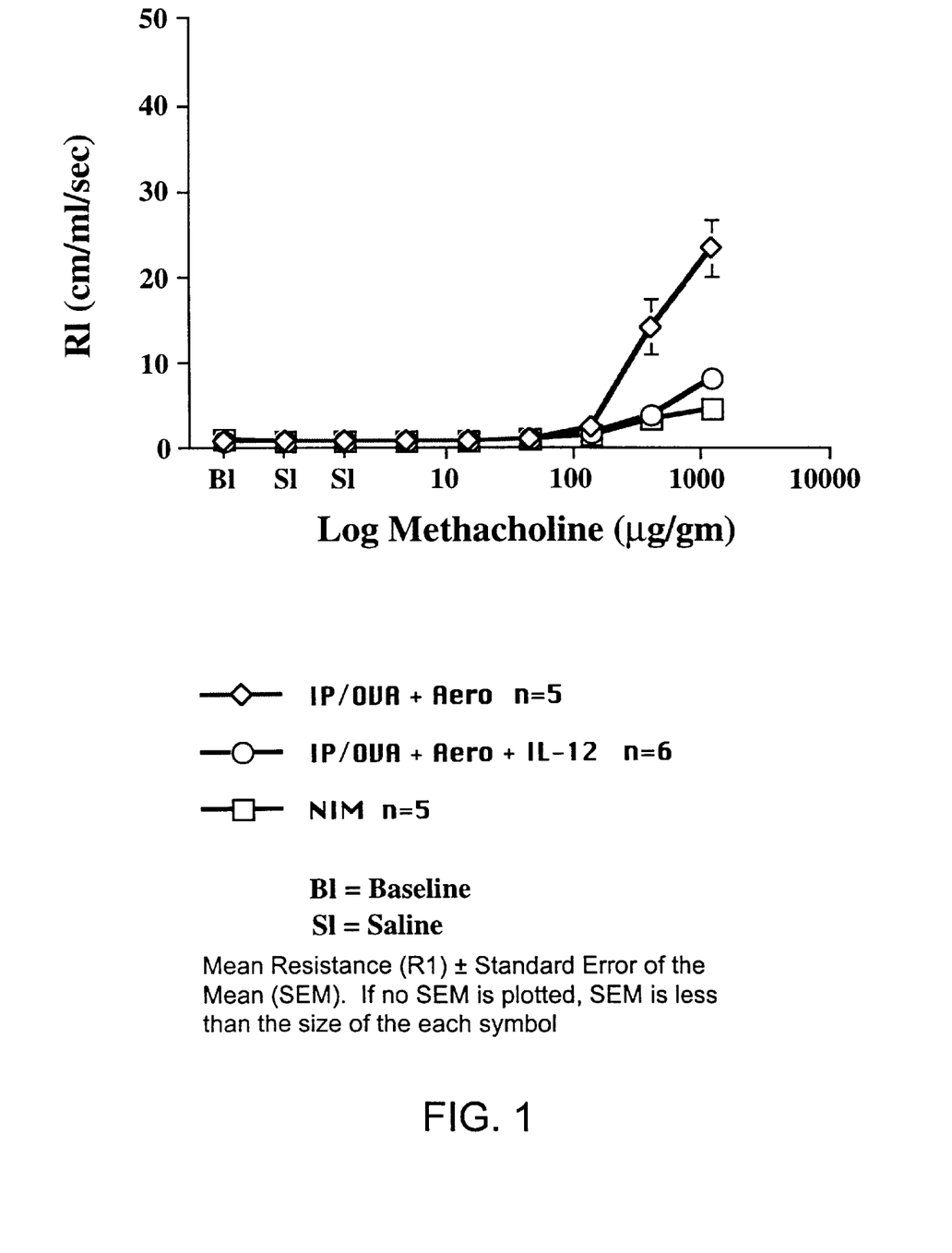
FIG. 1 illustrates the effect of IL-12 on the respiratory system function of a first group of BALB/c mice challenged with methacholine.

The means and standard errors of the log 10 of resistance (Rl) by dose of methacholine and by group obtained from the stress test are illustrated in FIG. 1 (n=the number of mice in each treatment group). The results indicate that administration of IL-12 to the OVA sensitized mice significantly blocks airway hyperresponsiveness to methacholine challenge. It should be noted that measuring the Rl value in a mouse, can be used to diagnose airflow obstruction similar to measuring the $FEV_1$, and/or $FEV_1/FVC$ ratio in a human.

B. Experiment 2

Figure 2:
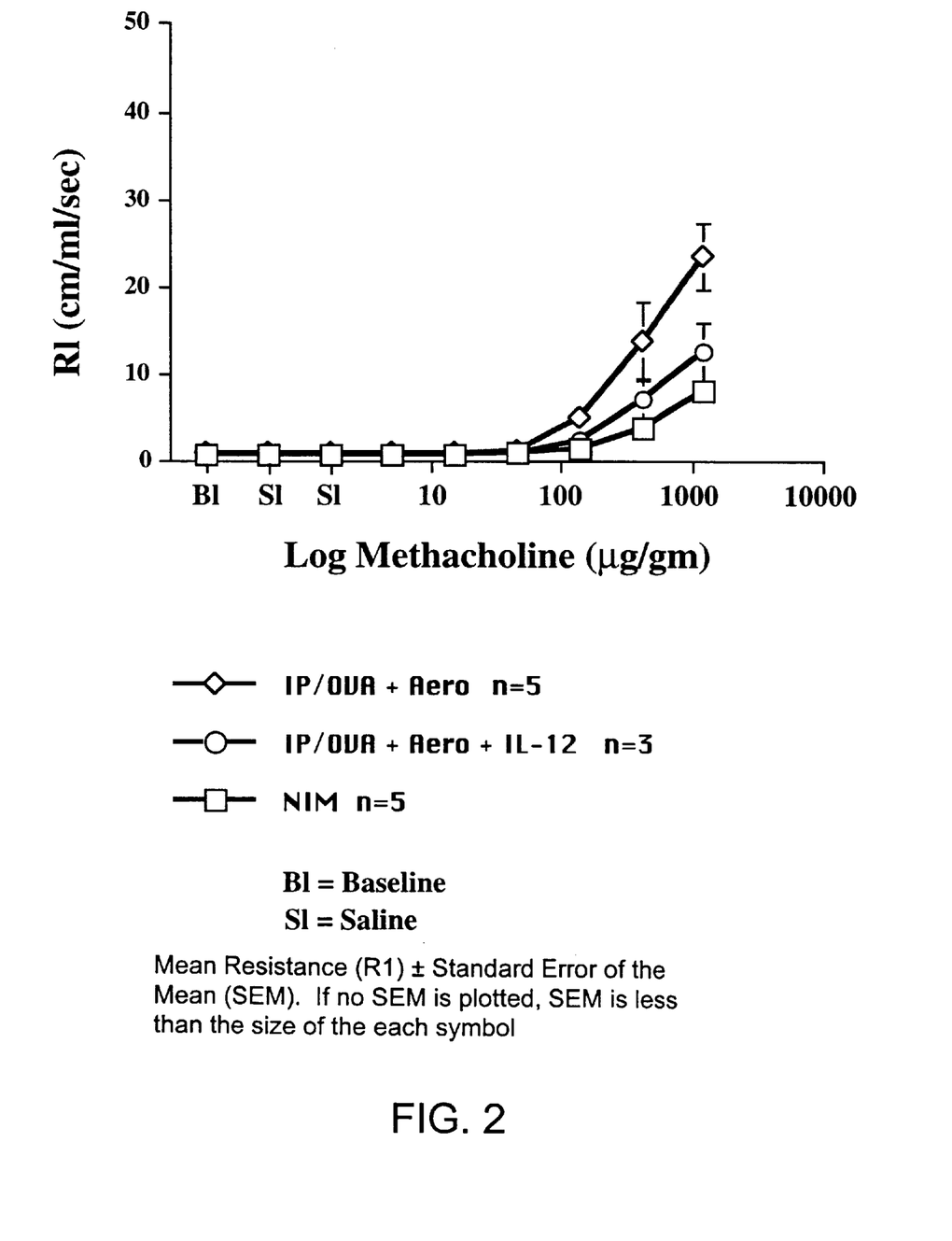
FIG. 2 illustrates the effect of IL-12 on the respiratory system function of a second group of BALB/c mice challenged with methacholine.

A separate set of mice were prepared as described above in Section A but on a different day. Eight mice were injected IP with OVA and treated with 1% aerosolized solution of OVA in PBS as described in section A. Five non-immune mice were prepared as described in section A. The 8 OVA-treated mice were challenged with methacholine using the method described above in Section A. The results of this second experiment are illustrated in FIG. 2 and are statistically identical to the results of Experiment 1 (Section A), thereby confirming the results of Experiment 1.

C. Combined Analysis

Figure 3:
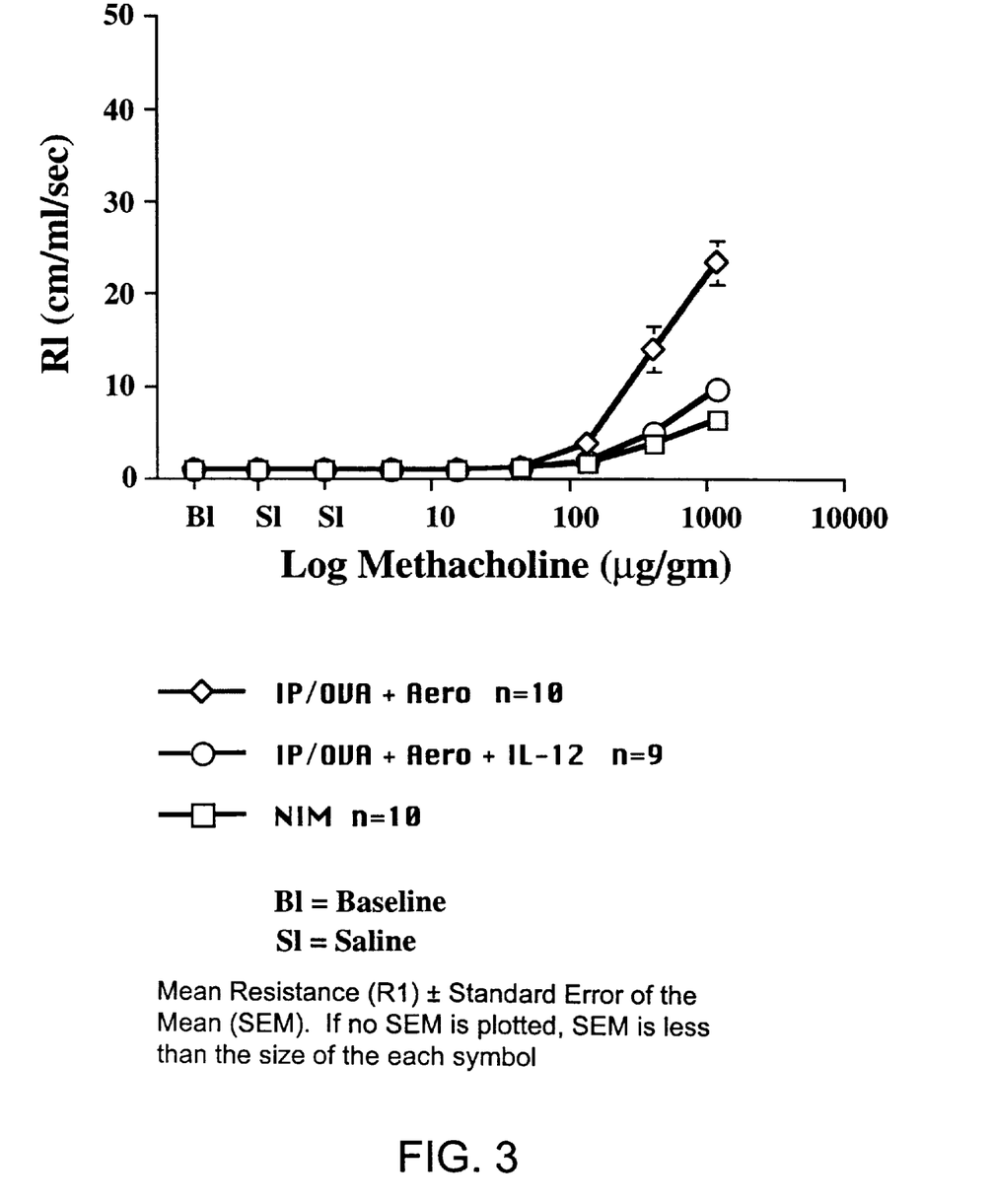
FIG. 3 illustrates the combined standard mean effect of IL-12 on the respiratory system function of a first and a second group of BALB/c mice challenged with methacholine.

A statistical analysis of the data was performed on the log 10 of resistance using Akaike Information Criteria repeated analysis variance. The repeated measures analysis of variance model with the unstructured variance matrix and fixed effects for group, dose and interaction of group by dose resulted in a significant interaction of p=0.0001. For each dose of methacholine, analysis of variance (ANOVA) was performed allowing for unequal variances. Pairwise comparisons were performed only if the ANOVA was significant for the given dose. The procedure used is an extension of Fisher's protected least significant difference multiple comparison procedure. Rl value for baseline, saline 1, saline 2 and each dose of methacholine±the standard error of the mean (SEM) are shown below in Table 1. The statistical values summarized in Table 1 are represented in FIG. 3.

TABLE I

MEANS AND STANDARD ERROR OF THE LOG MEAN RESISTANCE ($CM_{H2O/ML/SEC}$) BY IV METHACHOLINE (μg/gram)

| | | | Baseline | 5.08 | 15.23 | 45.68 | 137.04 | 411.07 | 1233.21 |
|---|---|---|---|---|---|---|---|---|---|
| 1 | NIM | MEAN | −.013 | −0.14 | −0.11 | 0.01 | 0.40 | 1.26 | 1.79 |
| | | STDERR | 0.05 | 0.05 | 0.05 | 0.05 | 0.07 | 0.09 | 0.2 |
| | | N | 10 | 10 | 10 | 10 | 10 | 10 | 10 |
| 2 | IP/OVA + AERO | MEAN | −0.09 | −0.09 | −0.04 | 0.18 | 1.14 | 2.48 | 3.10 |
| | | STDERR | 0.04 | 0.04 | 0.04 | 0.05 | 0.19 | 0.20 | 0.12 |
| | | N | 10 | 10 | 10 | 10 | 10 | 10 | 10 |
| 3 | IP/OVA + AERO +IL-12 | MEAN | −0.11 | −0.11 | −0.08 | 0.05 | 0.62 | 1.51 | 2.20 |
| | | STDERR | 0.03 | 0.03 | 0.02 | 0.04 | 0.11 | 0.15 | 0.13 |
| | | N | 9 | 9 | 9 | 9 | 9 | 9 | 9 |
| SIGNIFICANT CONTRASTS BY REPEATED ANALYSIS OF VARIANCE USING AKAIKE INFORMATION CRITERIA | | | NONE | NONE | NONE | 2 vs 1 | 2 vs 1 2 vs 3 | 2 vs 1 2 vs 3 | 2 vs 1 2 vs 3 1 vs 3 |

= number of mice/group
Saline 1 and Saline 2 not included

The results indicate that the pairwise comparison listed in the Akaike Information Criteria analysis were found to be significant, p<0.05. The overall p value using repeated analysis of variance is highly significant at p=0.0001. The results also indicate that over a 5-fold increase in AHR to methacholine following OVA immunization in BALB/c mice occurred. Administration of IL-12 blocks about 80% of the increase in OVA-induced AHR. Thus, IL-12 is a potent inhibitor of antigen induced AHR.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed:

1. A formulation for protecting an animal from a disease involving allergic inflammation, comprising interleukin-12 and an allergen.

2. The formulation of claim 1, wherein said formulation comprises a pharmaceutically acceptable excipient.

3. The formulation of claim 1, further comprising a controlled release vehicle selected from the group consisting of biocompatible polymers, other polymeric matrices, capsules, microcapsules, microparticles, bolus preparations, osmotic pumps, diffusion devices, liposomes, lipospheres, and transdermal delivery systems.

* * * * *